United States Patent
Zhan et al.

(10) Patent No.: US 8,664,191 B2
(45) Date of Patent: Mar. 4, 2014

(54) USE OF TWO MICRORNA MOLECULARS IN LUNG CANCER PROGNOSIS AND MEDICINE PREPARATION

(75) Inventors: Qimin Zhan, Beijing (CN); Lühua Wang, Beijing (CN); Nan Bi, Beijing (CN); Yongmei Song, Beijing (CN); Jianzhong Cao, Beijing (CN); Wenyang Liu, Beijing (CN)

(73) Assignee: Cancer Institute, Chinese Academy of Medical Services (CN)

( * ) Notice: Subject to any disclaimer, the term of this patent is extended or adjusted under 35 U.S.C. 154(b) by 0 days.

(21) Appl. No.: 13/382,686

(22) PCT Filed: Jul. 9, 2009

(86) PCT No.: PCT/CN2009/072695
§ 371 (c)(1),
(2), (4) Date: Mar. 19, 2012

(87) PCT Pub. No.: WO2011/003237
PCT Pub. Date: Jan. 13, 2011

(65) Prior Publication Data
US 2012/0220644 A1 Aug. 30, 2012

(51) Int. Cl.
*A61K 48/00* (2006.01)
*C12Q 1/68* (2006.01)
*C07H 21/02* (2006.01)
*C07H 21/04* (2006.01)

(52) U.S. Cl.
USPC ............... 514/44; 435/6; 536/23.1; 536/24.5

(58) Field of Classification Search
None
See application file for complete search history.

(56) References Cited

FOREIGN PATENT DOCUMENTS

| CN | 101031657 | 9/2007 |
| CN | 101400361 | 4/2009 |

OTHER PUBLICATIONS

"International Application No. PCT/CN2009/072695, International Search Report mailed Apr. 15, 2010", 14 pgs.

*Primary Examiner* — Amy Bowman
(74) *Attorney, Agent, or Firm* — Schwegman, Lundberg & Woessner, P.A.

(57) ABSTRACT

The present invention relates to use of two microRNAs in detection of lung cancer prognosis and in medicine preparation. Particularly, the invention relates to a composition comprising two small RNA molecules microRNA-150 and microRNA-886-3p, a device comprising the composition used in detection of lung cancer prognosis and in preparation of medicaments for inhibiting mammal and human lung cancer metastasis. Specifically, the expression levels of microRNA-150 and microRNA-886-3p can be used as the prognostic criteria of lung cancer prognosis, wherein high expression level of the gene combination indicates favorable therapeutic effect. The invention also relates to a device detecting the expression levels of microRNA-150 and microRNA-886-3p in mammalian and human lung cancer and a method for detecting the expression levels of microRNA-150 and microRNA-886-3p in samples.

7 Claims, 6 Drawing Sheets

US 8,664,191 B2

USE OF TWO MICRORNA MOLECULARS IN LUNG CANCER PROGNOSIS AND MEDICINE PREPARATION

PRIORITY CLAIM TO RELATED APPLICATIONS

This application is a national stage application under 35 U.S.C. §371 of PCT/CN2009/072695, filed Jul. 9, 2009, and published as WO 2011/003237 A1 on Jan. 13, 2011, which application and publication are incorporated by reference as if reproduced herein and made a part hereof in their entirety, and the benefit of priority of is claimed herein.

TECHNICAL FIELD

The invention relates to a composition including two microRNA molecules microRNA-150 and microRNA-886-3p, a device containing the composition for detecting prognosis of lung cancer and a use of the composition in the preparation of medicaments for inhibiting mammalian and human lung cancer transformation. Specifically, the expression level of microRNA-150 and microRNA-886-3p can be used as a prognostic marker in lung cancer, wherein, high expression of the gene combination in the test sample indicates good therapeutic effect. The invention also relates to a device for detecting the expression level of microRNA-150 and microRNA-886-3p in mammalian and human lung cancer patients and a method for detecting the expression level of microRNA-150 and microRNA-886-3p in the samples to be tested.

BACKGROUND OF THE INVENTION

Molecular biology techniques can be employed for an effective detection at molecular level to predict prognosis in patients with malignant tumor, and then, for a proper individual treatment of these diseases. Lung cancer is a common cancer worldwide, the incidence rate in male is 18%, while 21% in female. In 2005, approximate 500,000 new cases of lung cancer occurred in China (about 330,000 cases for male and 170,000 cases for female). The mortality of lung cancer is high, over 900,000 patients die from lung cancer each year (Parkin D M 1999). Therein, 15-20% of lung cancer cases are due to small cell lung cancer. Compared to non small cell lung cancer, small cell lung cancer is of unique morpha, substructure, immunohistochemical features and is classified as a kind of neuroendocrine tumors (Morita T 1990). The disease progresses rapidly, meanwhile, it is sensitive to the first course of radiotherapy and chemotherapy and the response rate is up to 60-80%, but it relapses soon after the treatment, and then becomes resistant to radiotherapy and chemotherapy. Only the patients who have small cell lung cancer at 15-25% limited stage and less than 5% extensive stage survive another five years via the treatment (Sandler A B 2003). In addition, 25-40% of the patients having small cell lung cancer are more than 70 years old at diagnosis. The patients poorly tolerate the chemotherapy because of complications and the like, and are badly prognosticated due to the limited treatment means, so their median survival time is only 10 months (Sekine I 2004). Therefore, there is an urgent need to develop a new treatment strategy which can improve the prognosis of small cell lung cancer.

Molecular targeted therapy has been a hot research point in recent years, and has made a breakthrough in treatment of some malignant tumors. For example, Gefinitib (Iressa) was used in non small cell lung cancer treatment, and the prognosis was good, especially for those patients who are female, do not smoke and suffer from adenocarcinoma; and Imatinib was used in treatment of gastrointestinal stromal tumors, and the better therapeutic effect had been obtained especially for those with Kit exon 11 mutations (Nilsson B 2007); and a combination of C225 and radiotherapy was employed in treatment of locally advanced head and neck cancer, and the survival rate was increased nearly 1 time than that of using radiotherapy alone (Bonner J A 2006). Therefore, it will be a great help for improving patient's prognosis to further understand the molecular mechanism of small cell lung cancer. Fischer et al. (Fischer B 2007) summarized the molecular mechanism studies of small cell lung cancer in recent 20 years: the molecular pathways involved in small cell lung cancer consist of mainly two pathways, PI3K/Akt/mTOR and RAS/MAPK, which are activated through binding of the cell surface receptor tyrosine kinases (RTKs) and their corresponding extracellular growth factors, wherein the RTKs mainly include IGF-IR, EGFR, VEGFR, PDGFR, c-MET. Thus, theoretically, inhibition of the growth of small cell lung cancer can be achieved through inhibition of RTKs or key targets in the pathways. However, it is a pity that no desired clinical effect has been obtained yet. In view of this, it may be a breakthrough for treatment to understand other aspects of the molecular mechanisms in small cell lung cancer.

Small RNA molecule (MicroRNA) generally consists of 18-25 nucleotides, which is a non-coding RNA molecule and can inhibit mRNA function and regulate translation process by binding to said target mRNA. Since 2005, a small amount of literatures on the relationship of microRNA and prognosis have been published, and have confirmed in chronic lymphoma, acute myeloid leukemia, non-small cell lung cancer, pancreatic cancer and neuroblastoma, colon cancer, that prognosis is significantly influenced by microRNA. However, studies on the effects of microRNA on the prognosis of small cell lung cancer have not yet been reported.

MicroRNA-150 (miR-150 for short), containing 22 nucleotides, locates on chromosome 19 and its sequence is shown as SEQ ID NO. 1: 5'-UCUCCCAACCCUUGUACCAGUG-3', with GenBank accession No. NT_011109.15, (sequence 22272232~22272315), which is commonly expressed in mature lymphocytes. As reported by Xiao C in 2007, the main function of microRNA-150 is to control the growth and differentiation of B lymphocytes by regulating c-Myb transcription factor. MicroRNA-886-3p (miR-886-3p for short), containing 21 nucleotides, locates on chromosome 5, and its sequence is shown as SEQ ID No. 2: 5'-CGCGGGUGCU-UACUGACCCUU-3', with GenBank accession No. NT_034772.5 (sequence 3783,1310~3783,1190), the function of which has not been reported in the literature.

SUMMARY OF THE INVENTION

Therefore, the first aspect of the present invention relates to a composition comprising a therapeutically effective amount of two microRNA molecules of microRNA-150 and microRNA-886-3p, wherein the sequences of microRNA-150 and microRNA-886-3P are shown as SEQ ID NO. 1: 5'-UCUCCCAACCCUUGUACCAGUG-3' and SEQ ID NO. 2: 5'-CGCGGGUGCUUACUGACCCUU-3', respectively. More particularly, the composition also includes a preservative for prevention of the degradation of microRNA molecules and a pharmaceutically acceptable carrier.

The second aspect of the present invention relates to a device containing the composition as described in the first aspect used for the detection of lung cancer prognosis. Specifically, the expression level of microRNAs, microRNA-150 and microRNA-886-3p, can be used as a criteria in the prognosis of lung cancer, in that high expression of the two microRNAs indicates a good prognosis for patients. More particularly, said lung cancer is small cell lung cancer. More particularly, said device is a gene chip or a reagent kit.

The third aspect of the present invention relates to use of the composition as described in the first aspect in preparation of medicaments for inhibiting mammalian and human lung cancer transformation. Particularly, said lung cancer is small cell lung cancer.

The fourth aspect of the present invention relates to a reagent kit for detecting expression status of microRNAs of microRNA-150 and microRNA-886-3P in mammalian and human lung cancer patients, comprising the followings:

1) Optionally, the reagents used for extracting microRNA from the patients,

2) SEQ ID NO.3, used as a primer of microRNA reverse transcription:

```
5'-GTGCAGGGTCCGAGGT-3',
```

3) a universal sense primer of microRNA:

```
SEQ ID NO. 4:
5'-GTCGTATCCAGTGCAGGGTCCGAGGTATTCGCACTGGATACGACC

ACTGG-3',
(for microRNA-150)

SEQ ID NO. 5:
5'-GTCGTATCCAGTGCAGGGTCCGAGGTATTCGCACTGGATACGACA

AGGGT-3',
(for microRNA-886-3p)
```

4) a specific antisense primer of microRNA

```
SEQ ID NO.6:
5'-GTCTCCCAACCCTTGTACCA-3',
(for microRNA-150)

SEQ ID NO.7:
5'-CACGCGGGTGCTTACTGAC-3',
(for microRNA-886-3p)
```

5) Optionally, other necessary reagents used for reverse transcription PCR or PCR, and 6) Optionally, other reagents used for detection of said microRNA, reverse transcription PCR products or PCR products, wherein the sequences of microRNA-150 and microRNA-886-3P are respectively shown as SEQ ID NO. 1 and SEQ ID NO. 2. Particularly, said device is a gene chip or a reagent kit.

The fifth aspect of the present invention relates to a method for detecting expression status of microRNA-150 and microRNA-886-3p in the samples to be tested, comprising the steps of:

1) Extracting microRNA from freshly isolated tissues or formalin-paraffin-embedded tissues, 2) Detecting tumor tissue specimens by means of gene chips, and screening genes associated with prognosis: microRNA-150 and microRNA-886-3p, 3) Processing the data from chips, comprising:

Evaluating the relationship between each microRNA signal expression value and survival rate by means of univariate Cox regression model;

Assigning each patient a compound value, via a linear combination of the statistically significant signal values of the microRNAs multiplied by the regression coefficients derived from the univariate Cox regression analyses;

Evaluating prognosis, using the median compound value as the cut-off point, with the formula of:

Compound value=0.545×(expression value of microRNA-150)+0.617×(expression value of microRNA-886-3$p$), 4) Verifying the prognostic model, wherein PCR amplification is performed with primers designed according to microRNA-150 and microRNA-886-3p gene sequences, and 2~4 μl of PCR products is detected by 1.5% non-denaturing agarose gel electrophoresis (without formaldehyde), 5) Collecting and processing PCR data:

Data are normalized using U6 RNA as an internal standard, and the prognosis is evaluated with the model built with chips.

In other words, the inventor studies on lung cancer, especially small cell lung cancer in China by means of microRNA gene chips and qRT-PCR techniques. Unexpectedly, the expression levels of microRNA-150 and microRNA-883-3p are different in the tissue samples from patients with different prognosis. Most patients with good prognosis have high expression of the two microRNAs. It is particularly important that after a linear combination of the signal values of the two microRNAs, the expression is more closely related to prognosis. Detection was carried out in another set of samples and similar results was obtained. Therefore, a combination of the genes can be used as a good prognostic model for lung cancer, especially for small cell lung cancer. With this model, lung cancer can be classified into two types, indolent and invasive, and different therapeutical regimens which will be employed depend on different types. Indolent lesions can be treated by using local treatment such as surgery, radiotherapy, and the treatment is relatively more aggressive for invasive lesions, mainly through systemic chemotherapy. By applying the gene combination to a corresponding gene chip or reagent kit, the prognosis can be rapidly known for lung cancer, especially for small cell lung cancer, in mammals including human beings, which will be of epoch-making significance in changing the therapeutical mode of lung cancer, especially small cell lung cancer.

In one embodiment of the invention, the effect of a composition containing microRNA-150 and microRNA-886-3p on the in vitro invasion and adhesion ability of lung cancer cell lines is described. The results show that microRNA-150 and microRNA-886-3p can diminish adhesive capacity of lung cancer cell to extracellular matrix and inhibit the invasive metastasis of lung cancer cells. Therefore, the microRNA molecules of microRNA-150 and microRNA-886-3p as mentioned in the invention have a potential in use for the treatment of lung cancer, especially small cell lung cancer.

In another embodiment of the invention, the detection method according to the present invention is described, which mainly comprises the steps of microRNA extraction, gene chip preparation, hybridization, and qRT-PCR verification and the like. Gene chip detection is mainly used for screening genes associated with prognosis. The genes which are screened out are verified by qRT-PCR. Since the inventor has found the genes associated with the prognosis of small cell lung cancer, it is feasible to use only microRNA extraction and qRT-PCR in future clinical applications. These two methods are conventional operations for those skilled in the art. Therefore, it is easy to clinically popularize the model.

In another embodiment of the invention, a method for detecting the expression status of microRNA-150 and microRNA-886-3p in the samples to be tested is also described, which comprises the following steps of:

1) Extracting microRNA from freshly isolated tissues or formalin paraffin embedded tissues, 2) Detecting tumor tissue specimens by means of gene chips, and screening genes associated with prognosis: microRNA-150 and microRNA-886-3p, 3) Processing the data from chips, comprising:

evaluating the relationship between each microRNA signal expression value and survival rate by means of univariate Cox regression model;

Assigning each patient a compound value, via a linear combination of the statistically significant signal values of the microRNAs multiplied by the regression coefficients derived from the univariate Cox regression analyses;

Evaluating prognosis, using the median compound value as the cut-off point, with the formula of:

Compound value=0.545×(expression value of microRNA-150)+0.617×(expression value of microRNA-886-3$p$), 4) Verifying the prognostic model, wherein PCR amplification is performed with primers designed according to microRNA-150 and microRNA-886-3p gene sequences, and 2~4 μl of PCR products is detected by 1.5% non-denaturing agarose gel electrophoresis (without formaldehyde), and 5) Collecting and processing PCR data:

Data are normalized using U6 RNA as an internal standard, and the prognosis is evaluated with the model built with chips.

DETAILED DESCRIPTION OF THE DRAWINGS

FIG. 1 shows the electrophoresis results of microRNA-150 and microRNA-886-3p from small cell lung cancer tissues, wherein 1~40 hsa-miR-let-7i gene is amplified by RealTime PCR, respectively using 1st-cDNA of sample 145, 146, 147, 148, 151, 152, 156, 157, 158, 160, 162, 163, 165, 167, 168, 169, 170, 172, 174, 176, 177, 178, 179, 180, 181, 182, 183, 184, 186, 188, 189, 192, 195, 195, 196, 197, 198, 199, 200 and 202 as the template;

41~80 hsa-miR-150 gene is amplified by RealTime PCR, respectively using 1st-cDNA of sample 145, 146, 147, 148, 151, 152, 156, 157, 158, 160, 162, 163, 165, 167, 168, 169, 170, 172, 174, 176, 177, 178, 179, 180, 181, 182, 183, 184, 186, 188, 189, 192, 195, 195, 196, 197, 198, 199, 200 and 202 as the template;

81~120 hsa-miR-886-3p gene is amplified by RealTime PCR, respectively using 1st-cDNA of sample 145, 146, 147, 148, 151, 152, 156, 157, 158, 160, 162, 163, 165, 167, 168, 169, 170, 172, 174, 176, 177, 178, 179, 180, 181, 182, 183, 184, 186, 188, 189, 192, 195, 195, 196, 197, 198, 199, 200 and 202 as the template.

Molecular weight marker: TaKaRa DL2000, sizes of marker DNAs comprising 100 bp, 250 bp, 500 bp, 750 bp, 1000 bp, 2000 bp (from bottom to top)

As indicated in the results of electrophoresis, there is a good specificity in the microRNA RealTime PCR reaction.

Figure 5:
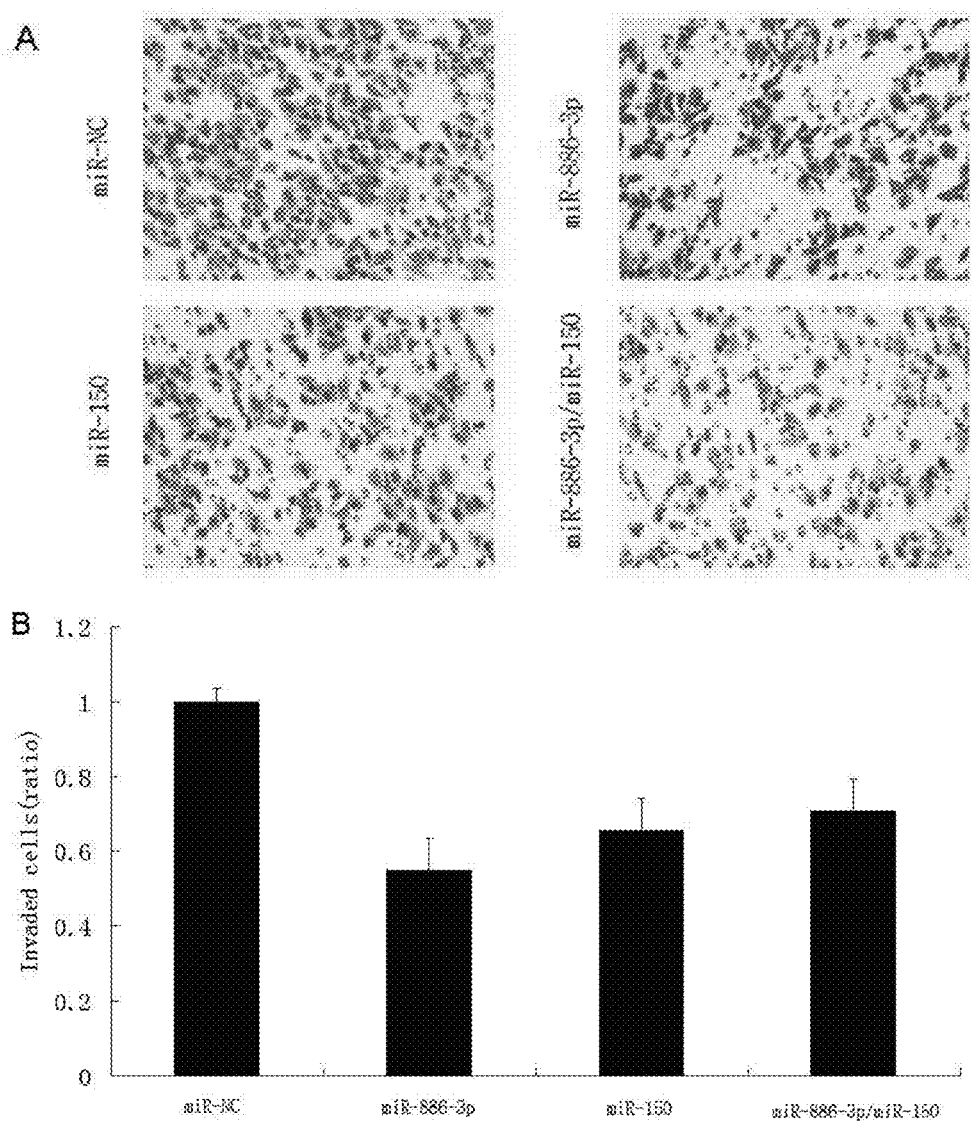

FIG. 5 shows that microRNA-886-3p and microRNA-150 inhibit the in vitro invasion ability of the cells, A: The schematic diagram of cell staining shows the inhibition of in vitro invasion ability of H446 cells after miR control, miR-150, miR-886-3p, miR-150/miR-886-3p was respectively added to the cell line, B: The histogram shows the inhibition of in vitro invasion ability of H446 cells after miR control, miR-150, miR-886-3p, miR-150/miR-886-3p was respectively added to the cell line.

Figure 6:
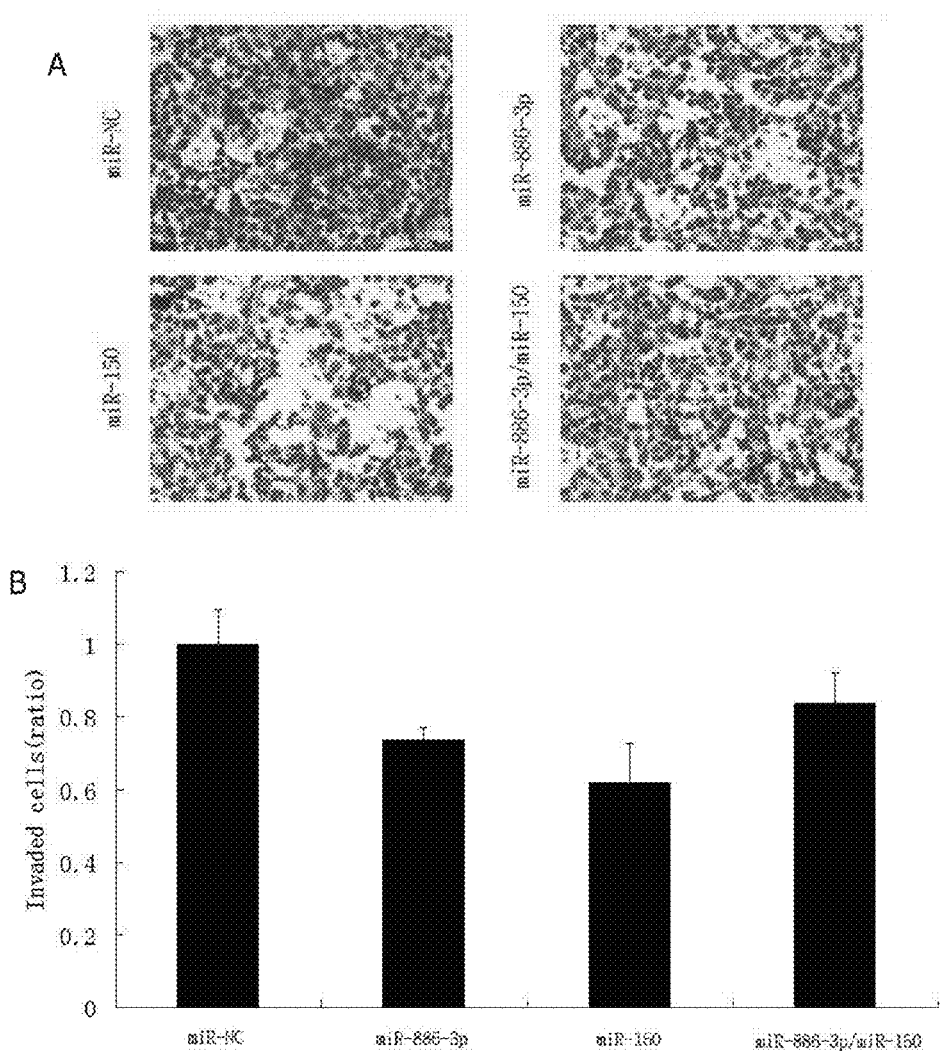

FIG. 6 shows that microRNA-886-3p and microRNA-150 inhibit the in vitro invasion ability of the cells, A: The schematic diagram of cell staining shows the inhibition of in vitro invasion ability of H1299 cells after miR control, miR-150, miR-886-3p, miR-150/miR-886-3p was respectively added to the cell line, B: The histogram shows the inhibition of in vitro invasion ability of H1299 cells after miR control, miR-150, miR-886-3p, miR-150/miR-886-3p was respectively added to the cell line.

Figure 7:
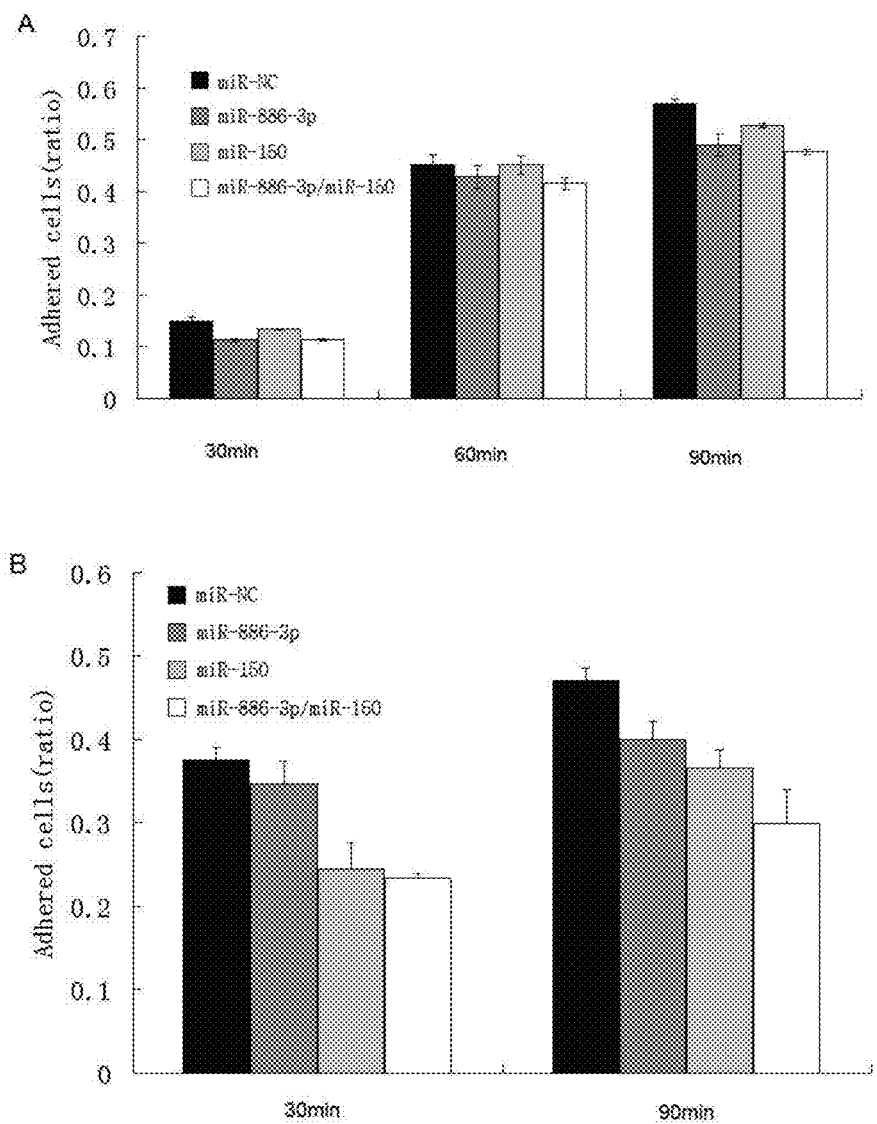

FIG. 7 shows that microRNA-886-3p and microRNA-150 inhibit the cell adhesion to matrix, A: The histogram shows the adhesion rate of H446 cells at 30, 60, 90 minutes post miR-NC (control), miR-886-3p, miR-150, miR-886-3p/miR-150 transfection, B: The histogram shows the adhesion rate of H1299 cells at 30, 90 minutes post miR-NC (control), miR-886-3p, miR-150, miR-886-3p/miR-150 transfection.

DETAILED DESCRIPTION OF THE INVENTION

The present invention will be further described by use of the following examples, but not limited to these ones.

In the following examples, unless specifically indicated, all the reagents used in the application are analytically pure and commercially available. Unless otherwise indicated, RT-PCR, PCR and other operations as mentioned in the examples of the invention are performed in accordance with "Molecular Cloning: a Laboratory Manual (The 3rd Edition)" (J. Sambrook and D. W. Russell [USA], translated by Peitang Huang et al, Science Press, 2002) and the manufacturer's instruction; cell culture, cell passage, cell recovery and cryopreservation, cell transfection, immunofluorescence assay and other operations are carried out in accordance with "Culture of Animal Cells: a Manual of Basic Technique (The 4th Edition)" (R. Ian Freshney [UK], translated by Jingbo Zhang et al, Science Press, 2000) and the manufacturer's instruction.

Example 1

The Method for Detecting Gene Expression Status of MicroRNA-150 and MicroRNA-886-3p 1. Extraction of Total RNA of Samples—Extraction of Total RNA from Tissues or Cells with Trizol Method (1) Sample Source Samples were collected from the Cancer Institute and Hospital, Chinese Academy of Medical Sciences and Peking Union Medical College. The inclusion criteria comprises: Age≤75; KPS scores≥80; The patients with small cell lung cancer in limited stage, receiving surgery±chemotherapy±radiotherapy; Sufficient formalin-paraffin-embedded tissues to obtain enough miRNA; Complete written medical records and follow-up records. 42 cases of formalin-fixed and paraffin-embedded small cell lung cancer specimens between 2002 and 2005 which met the inclusion criteria were chosen for the microRNA chip detection and screening of microRNAs associated with prognosis. 40 cases of formalin-fixed and paraffin-embedded small cell lung cancer specimens between 2000 and 2001 were chosen for verification of the chip results. The characteristics of specific cases are shown in table 1.

TABLE 1

The characteristics of specific cases

| Variable | | Chip group N = 42(%) | Verification group N = 40(%) | P value |
|---|---|---|---|---|
| Age(year) | Mean ± SD | 60.1 ± 11.1 | 54.3 ± 11.8 | 0.025 |
| | Range | 33~74 | 33~73 | |
| Gender | Male | 30(71.4) | 32(80.0) | |
| | Female | 12(28.6) | 8(20.0) | 0.445 |
| Smoking | Yes | 30(71.4) | 29(72.5) | |
| | No | 12(28.6) | 11(27.5) | 1.000 |
| Stage | I | 16(38.1) | 6(15.0) | |
| | II | 14(33.3) | 10(25.0) | 0.010 |
| | III | 12(28.6) | 24(60.0) | |
| Tumor location | Superior lobe | 25(59.5) | 21(52.5) | 0.657 |
| | Intermediate and inferior lobe | 17(40.5) | 19(47.5) | |
| Treatment | Surgery + chemotherapy | 39(92.9) | 32(80) | |
| | Surgery + chemotherapy + radiotherapy | 2(4.8) | 7(17.5) | 0.120 |
| | Surgery alone | 1(2.4) | 1(2.5) | |

(2) Sample Processing (Grinding is not Necessary for Bacteria or Cells)

The tissue sample with an area of about 1 cm$^2$ was broken in aluminum foil, then transferred to an Eppendorf tube containing steel beads and ground with a grinding mill (30 l/s, 8 min), note: This step should be operated as much as possible in a cryogenic liquid nitrogen environment, and grinding is not necessary for bacteria or cells;

(3) 1 ml of trizol was added into the Eppendorf tube after the grinding step, and mixed by shaking;

(4) The mixed solution was transferred to a new Eppendorf tube, and 200 μl of chloroform was added and mixed by shaking;

(5) The solution was centrifuged at 12000 rpm for 15 min at 4° C.

(6) The obtained supernatant was transferred to a new Eppendorf tube, and 500 μl of isopropanol was added, then gently mixed and placed for 15 min at room temperature;

(7) The solution was centrifuged at 12000 rpm for 15 min at 4° C.

(8) The supernatant was removed, and then 1 ml of 75% ethanol was added and mixed by shaking;

(9) The solution was centrifuged at 7500 rpm for 5 min at 4° Q

(10) The supernatant was removed, and the ethanol was totally evaporated in a laminar flow cabinet;

(11) 40~60 μl of DEPC H$_2$O was added, and the mixture was solubilized at 65° C. for 5 min;

(12) The obtained sample was frozen at −20° C. for cryopreservation.

2. Quality Assessment of Total RNA (1) Determination of total RNA concentration by Nanoprop (loading 2 μl of total RNA), (2) Determination of RNA quality by means of 1.5% formaldehyde denaturing agarose gel electrophoresis

| | | |
|---|---|---|
| Total RNA | | 500 ng |
| 5 × Loading Buffer | μl | 2 |
| DEPC H$_2$O | | to 8~9 μl |
| The mixture was denatured at 65° C. for 5 min, then put into an ice bath for 5 min | | |
| EB(500-fold dilution) | | 1 μl |

The total volume is about 6~8 μl.

Formaldehyde denaturing agarose gel: 0.45 g of agarose was added into 30 ml of 1×TBE Buffer, the mixture was heated to melt in a microwave oven and gently shaken to mix the agarose thoroughly (no suspending granules can be visually observed), 600 μl of formaldehyde was added when the mixture cooled to about 60° C., mixed, and then poured into a special gel casting module for RNA (7.5×5.5 cm). After being placed for about 30 min at room temperature, the agarose gel would be ready to use.

The electrophoresis was performed at 120~130V for 15~20 min

Figure 4:
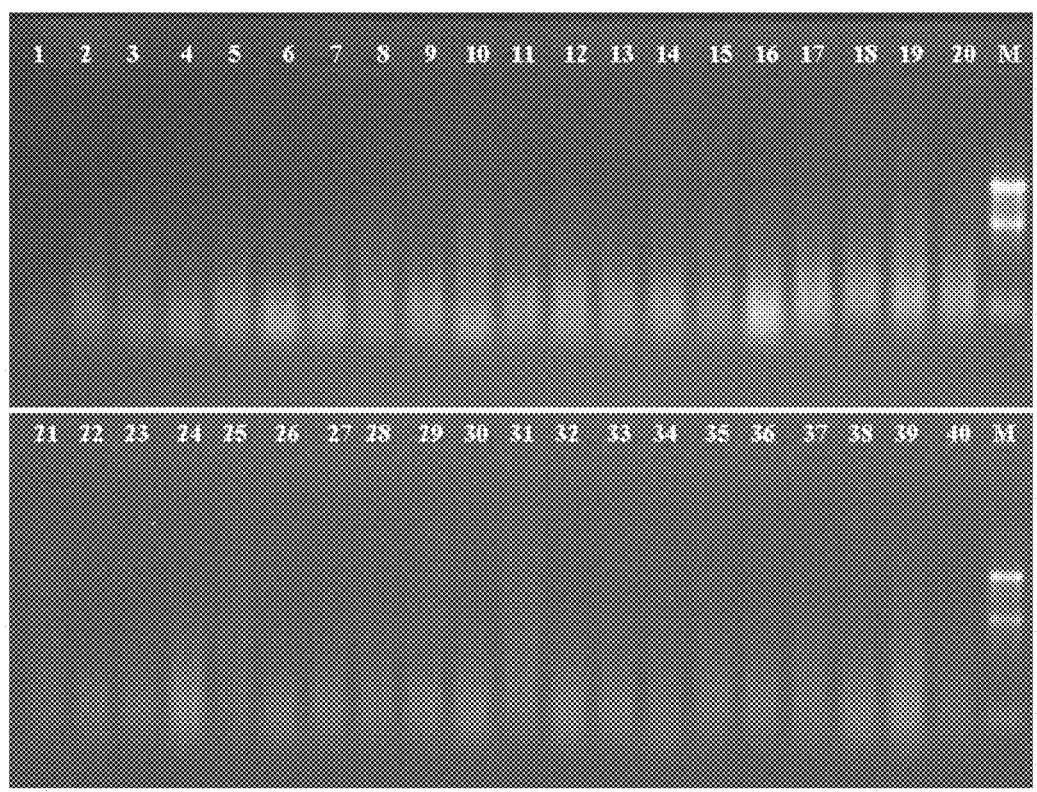
FIG. 4 shows the verification of RNA extraction in table 1.

The quantity, degradation and size of the RNAs extracted from the 40 specimens in the invention are shown in table 2 and FIG. 4.

TABLE 2

The vertification of RNA

| Lane | A$_{260}$ | A$_{280}$ | A$_{260/280}$ | A$_{260/230}$ | Concentration (ng/μl) | Total amount (μg) | Results of electrophoresis |
|---|---|---|---|---|---|---|---|
| 1 | 62.489 | 34.048 | 1.84 | 2.26 | 2499.56 | 499.912 | RNA degradation |
| 2 | 8.054 | 4.766 | 1.69 | 1.93 | 322.14 | 64.428 | RNA degradation |
| 3 | 95.425 | 52.686 | 1.81 | 2.17 | 3817 | 763.4 | RNA degradation |
| 4 | 65.457 | 35.985 | 1.82 | 2.19 | 2618.27 | 523.654 | RNA degradation |
| 5 | 11.611 | 6.536 | 1.78 | 2.18 | 464.43 | 92.886 | RNA degradation |
| 6 | 57.839 | 31.169 | 1.86 | 2.05 | 2313.57 | 462.714 | RNA degradation |
| 7 | 113.089 | 67.862 | 1.67 | 2.01 | 4523.56 | 904.712 | RNA degradation |
| 8 | 69.717 | 37.33 | 1.87 | 2.21 | 2788.69 | 557.738 | RNA degradation |
| 9 | 31.285 | 17.133 | 1.83 | 2.32 | 1251.39 | 250.278 | RNA degradation |

TABLE 2-continued

The vertification of RNA

| Lane | $A_{260}$ | $A_{280}$ | $A_{260/280}$ | $A_{260/230}$ | Concentration (ng/μl) | Total amount (μg) | Results of electrophoresis |
|---|---|---|---|---|---|---|---|
| 10 | 103.177 | 57.997 | 1.78 | 2.17 | 4127.07 | 825.414 | RNA degradation |
| 11 | 83.719 | 45.835 | 1.83 | 2.31 | 3348.76 | 669.752 | RNA degradation |
| 12 | 70.802 | 38.252 | 1.85 | 2.21 | 2832.08 | 566.416 | RNA degradation |
| 13 | 41.937 | 23.6 | 1.78 | 2.25 | 1677.49 | 335.498 | RNA degradation |
| 14 | 10.302 | 5.742 | 1.79 | 1.97 | 412.08 | 82.416 | RNA degradation |
| 15 | 63.282 | 35.251 | 1.8 | 2.3 | 2531.29 | 506.258 | RNA degradation |
| 16 | 9.169 | 5.158 | 1.78 | 2.02 | 366.75 | 73.35 | RNA degradation |
| 17 | 33.184 | 17.966 | 1.85 | 2.32 | 1327.37 | 265.474 | RNA degradation |
| 18 | 22.921 | 12.538 | 1.83 | 2.4 | 916.85 | 183.37 | RNA degradation |
| 19 | 14.606 | 8.118 | 1.8 | 2.36 | 584.25 | 116.85 | RNA degradation |
| 20 | 27.114 | 14.844 | 1.83 | 2.14 | 1084.56 | 216.912 | RNA degradation |
| 21 | 33.802 | 18.46 | 1.83 | 2.11 | 1352.08 | 270.416 | RNA degradation |
| 22 | 34.601 | 18.898 | 1.83 | 2.29 | 1384.05 | 276.81 | RNA degradation |
| 23 | 0.25 | 0.15 | 1.66 | 1.5 | 9.98 | 1.996 | RNA degradation |
| 24 | 10.171 | 5.778 | 1.76 | 1.99 | 406.84 | 81.368 | RNA degradation |
| 25 | 48.25 | 26.973 | 1.79 | 2.12 | 1929.99 | 385.998 | RNA degradation |
| 26 | 20.812 | 11.576 | 1.8 | 2.14 | 832.47 | 166.494 | RNA degradation |
| 27 | 11.803 | 6.701 | 1.76 | 2.23 | 472.12 | 94.424 | RNA degradation |
| 28 | 35.502 | 19.186 | 1.85 | 2.05 | 1420.09 | 284.018 | RNA degradation |
| 29 | 48.24 | 25.835 | 1.87 | 2.34 | 1929.6 | 385.92 | RNA degradation |
| 30 | 64.657 | 34.963 | 1.85 | 2.29 | 2586.28 | 517.256 | RNA degradation |
| 31 | 16.224 | 9.008 | 1.8 | 2.22 | 648.96 | 129.792 | RNA degradation |
| 32 | 29.56 | 16.061 | 1.84 | 2.2 | 1182.41 | 236.482 | RNA degradation |
| 33 | 45.883 | 24.671 | 1.86 | 2.21 | 1835.34 | 367.068 | RNA degradation |
| 34 | 27.885 | 15.132 | 1.84 | 2.25 | 1115.39 | 223.078 | RNA degradation |
| 35 | 35.712 | 18.743 | 1.91 | 2.14 | 1428.47 | 285.694 | RNA degradation |
| 36 | 13.813 | 7.397 | 1.87 | 2.2 | 552.5 | 110.5 | RNA degradation |
| 37 | 44.185 | 23.706 | 1.86 | 2.16 | 1767.42 | 353.484 | RNA degradation |
| 38 | 14.484 | 7.836 | 1.85 | 1.94 | 579.36 | 115.872 | RNA degradation |
| 39 | 33.135 | 18.072 | 1.83 | 2.12 | 1325.41 | 265.082 | RNA degradation |
| 40 | 42.151 | 23.146 | 1.82 | 2.24 | 1686.04 | 337.208 | RNA degradation |

3. Reverse Transcription of MicroRNA:
(1) Reaction System of Reverse Transcription

| | |
|---|---|
| Total RNA | 100 ng |
| Reverse transcription primer of microRNA: SEQ ID NO. | 1 μl(1 μM) |
| DEPC H$_2$O | to 12.3 μl |
| The mixture was denatured at 65° C. for 5 min, then put into an ice bath for 5 min. | |
| 5 × 1$^{st}$ Buffer | 4 μl |
| 0.1M DTT | 2 μl |
| dNTPs | 0.5 μl(10 mM for each) |

-continued

| | |
|---|---|
| RNase Inhibitor | 0.2 μl(40 U/μl) |
| M-MLV | 1 μl(200 U/μl) |

The total volume of the system was 20 μl.

(2) The Program of Reverse Transcription was: 16° C. for 30 min, 37° C. for 30 min, 70° C. for 10 min, and then the Products were Kept at 4° C. to be Used.

4. Realtime PCR Reaction of MicroRNA
(1) Reaction System of MicroRNA RealTime PCR

| | |
|---|---|
| Template(cDNA) 1 μl of the 20 μl reaction system of reverse transcription in general | |
| MgCl$_2$ | 1.6 μl |
| Primers: universal sense primer of microRNA | 0.6 μl (10 μM) |
| For microRNA-150: SEQ ID NO. 4 | |
| For microRNA-886-3p: SEQ ID NO. 5 | |
| Specific antisense primer | 0.6 μl (10 μM) |
| For microRNA-150: SEQ ID NO. 6 | |
| For microRNA-886-3p: SEQ ID NO. 7 | |
| DNA Master SYBR Green I MIX | 2 μl |
| Nuclease Free H$_2$O was added to 20 μl | |

(2) Program of MicroRNA RealTime PCR

| | | | |
|---|---|---|---|
| Enzyme activation: | 95° C., | 10 min | |
| Amplification reaction: | 95° C., | 15 s | denaturation |
| | 60° C., | 30 s | annealing, and elongation |
| | 74° C., | 3 s | fluorescence detection |
| 40 cycles in all, | | | |
| Melting curve: | 75~95° C. | | |

(3) Determination of RealTime PCR Product by Means of 1.5% Non-Denaturing (Formaldehyde Free) Agarose Gel Electrophoresis

| | |
|---|---|
| microRNA RealTime PCR products | 2~4 μl |
| 2 × Loading Buffer | 4 μl |

The total volume was about 6~8 μl.

Non denaturing agarose gel: 1.2 g of agarose was added into 80 ml of 1×TBE Buffer, the mixture was heated to melt in a microwave oven and gently shaken to mix the agarose thoroughly (no suspending granules can be visually observed), 2 μl of EB (stock solution) was added when the mixture cooled to about 60° C., the solution was mixed, and then poured into a gel casting module (15×15 cm). After being placed for about 30 min at room temperature, the agarose gel would be ready to use.

The electrophoresis was performed at 100V for 25-30 min.

Figure 1:
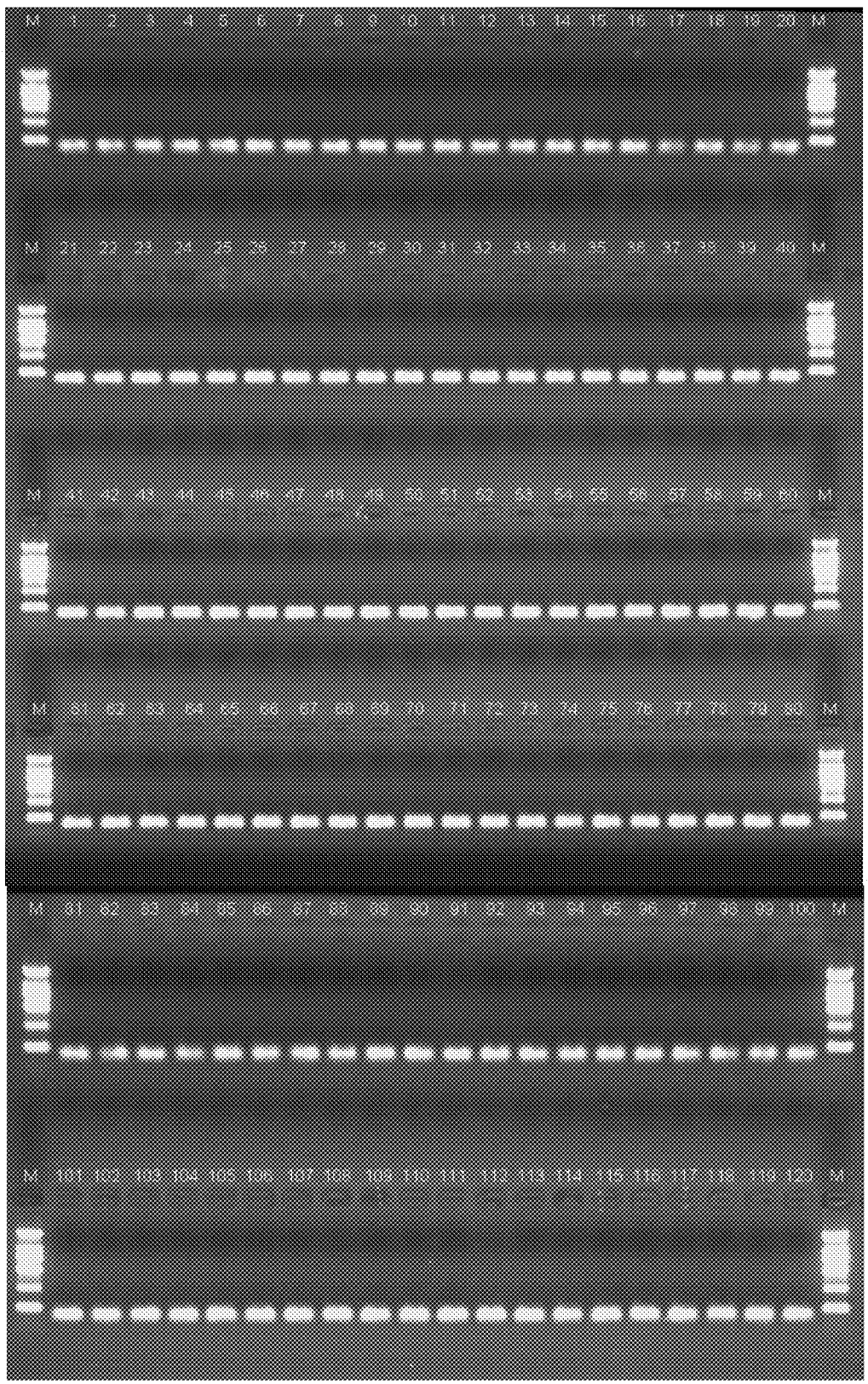

The results of electrophoresis shows a good specificity in microRNA RealTime PCR reaction, as shown in FIG. 1.

5. Data Collection and Processing

The expression values of microRNAs were converted into codes, wherein they were divided into three equal parts according to the expression levels thereof. The first one third part was given a code "1" which corresponded to the low expression level among the total expressions, the second one third part was given a code "2" which corresponded to the median expression level, and the last one third was given a code "3" corresponding to the high expression level. Then the code of each microRNA was introduced into a univariate Cox regression model to find the microRNAs associated with prognosis. Protective microRNAs for prognosis were defined as those with hazard ratio for death <1. Negative-associated microRNAs for prognosis were defined as those with hazard ratio for death >1[18]. After the univariate Cox proportional-hazards regression analysis was used to find microRNAs, the expression values of each microRNA were multiplied by the regression coefficients (B value) to form a linear combination used to be a prognosis risk score for each patient, wherein B value was given by the univariate Cox regression analysis. The formula was given as follows: Risk score=B1g1+B2g2+B3g3+ . . . +Bngn (B: regression coefficients, g: expression value of miRNA, n: number of miRNAs). Patients with higher risk score are expected to have poorer survival outcomes. Then patients in different groups including training group and testing group were divided into high-risk and low-risk groups using the median microRNA risk score as the cut-off point.

Figure 2:
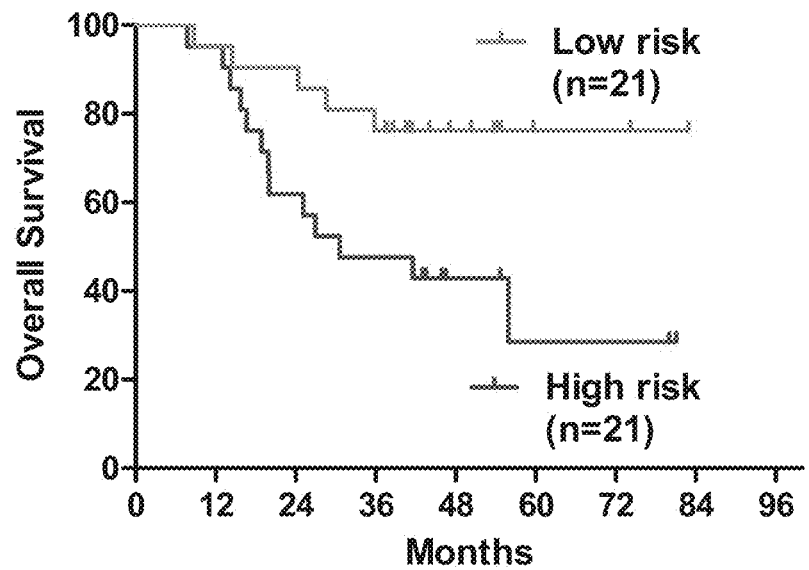
FIG. 2 shows that the prognosis of patients with small cell lung cancer in the chip group is analyzed according to the expression status of the prognostic model.
Figure 3:
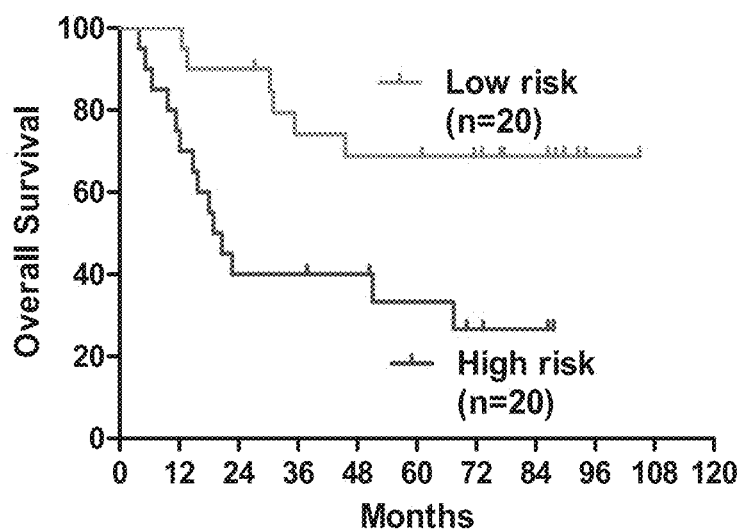
FIG. 3 shows that the prognosis of patients with small cell lung cancer in the PCR Verification group is analyzed according to the expression status of the prognostic model.

The Kaplan-Meier method was used to estimate overall survival. Differences in survival between the high-risk and the low-risk patients was analyzed. Data were normalized using U6 RNA as an internal standard. A univariate Cox regression model was used to analyze the relationship between the abundance value of each microRNA and the survival rate. A compound value was assigned to each patient according to a linear combination of the statistically significant signal value of the microRNAs derived from the univariate Cox regression analyses multiplied by the regression coefficients. The compound values were used to evaluate the prognosis of the patients. The patients were divided into two groups using the median microRNA compound value as the cut-off point, and the low-risk group had a longer survival time compared to high-risk group (P=0.005, see FIG. 2 and FIG. 3). As shown in FIG. 2, in the training group, the 3-year and 5-year survival of the high-risk group was 47.6% and 28.6% respectively, while the 3-year and 5-year survival of the low-risk group was 76.2%. As shown in FIG. 3, in the testing group, the 3-year and 5-year survival of the high-risk group was 40% and 33.6% respectively, while the 3-year and 5-year survival of the low-risk group was 74.1% and 68.8%.

Example 2

Study on the Biological Effect of MicroRNA-886-3p and MicroRNA-150 on Inhibiting the Invasion and Adhesion of Lung Cancer Cells 1. Experimental Procedures
(1) Cell Culture Human small cell lung cancer cell line NCI-H446 was purchased from the Cell Center of Basic Medical Sciences, Chinese Academy of Medical Sciences, and cultured in 1640 medium containing 10% fetal bovine serum at 37° C. in a 5% CO$_2$ atmosphere.

Human non small cell lung cancer cell line NCI-H1299 was kindly provided by professor Weiguo Zhu, Department of Biochemistry and Molecular Biology, Peking University Health Science Center, and cultured in 1640 medium containing 10% fetal bovine serum at 37° C. in a 5% CO$_2$ atmosphere.

(2) miRNA Transient Transfection a. Preparation of miRNA mother liquor: 250 μL 1× universal buffer was added into 5 nmol miRNA to obtain 20 μmol/L miRNA mother liquor, b. The well grown cells were inoculated in a 6-well plate (without antibiotics) on the day before transfection, and the transfection was carried out when the cell density reached about 70%, c. Preparation of the following complexes: Solution A: the miRNA at proper concentration was diluted into 250 μL of serum-free medium, and gently mixed. Solution B: 6 μL of Lipofectamine 2000, which had been mixed thoroughly before use, was diluted in 250 μL of serum-free medium, mixed, and incubated for 5 minutes at room temperature, d. The dilution of liposome (solution B) was gently mixed with the dilution of miRNA (solution A), and incubated for 20 minutes at room temperature, e. 500 μL of the mixed complexes was added into the 6-well plate. 2 mL of serum-free medium was added and then gently mixed. The original medium was removed after 6 hours, and replaced with RPMI 1640 medium containing 10% serum.

(3) miRNA Real-Time RT-PCR a. Extraction of total RNA of samples-extraction of total RNA from cells with Trizol method (I) The well grown cells were employed. When the cell density reached 80%-90%, the culture medium was poured out of the bottle, and the cells were washed twice with PBS;

(II) 1 ml of trizol was added into the bottle, gently shaken, and placed on ice for 15 minutes;

(III) The mixed solution was transferred to an Eppendorf tube pretreated with DEPC, and 200 μl of chloroform was added and mixed by shaking;

(IV) The solution was centrifuged at 12000 rpm for 15 min at 4° C.;

(V) The obtained supernatant was transferred to a new Eppendorf tube, 500 μl of isopropanol was added, gently mixed, then placed for 15 min at room temperature;

(VI) The solution was centrifuged at 12000 rpm for 15 min at 4° C.;

(VII) The supernatant was discarded, and then 1 ml of 75% ethanol was added and mixed by shaking;

(VIII) The solution was centrifuged at 7500 rpm for 5 min at 4° C.

(IX) The supernatant was discarded, and ethanol was totally evaporated in a laminar flow cabinet;

(X) 40~60 μl of DEPC $H_2O$ was added, and the pellets were solubilized at 65° C. for 5 min;

(XI) The obtained sample was frozen at −20° C. for cryopreservation.

b. Quality assessment of total RNA (I) Determination of total RNA concentration by Nanoprop (loading 2 μl of total RNA), (II) Determination of RNA quality by means of 1.5% formaldehyde denaturing agarose gel electrophoresis

| | |
|---|---|
| Total RNA | 500 ng |
| 5 × Loading Buffer | 2 μl |
| DEPC $H_2O$ | to 8~9 μl |
| The mixture was denatured at 65° C. for 5 min, then put into an ice bath for 5 min. | |
| EB(500-fold Dilution) | 1 μl |

The total volume is about 6~8 uL.

Formaldehyde denaturing agarose gel: 0.45 g agarose was added to 30 ml×TBE Buffer, heated to melt in a microwave oven, gently shaken to thoroughly mix the agarose (no suspended granules can be visually observed.), then 600 ul formaldehyde was added when cooled to about 60° C. and the solution was mixed and then poured into a special gel casting module for RNA (7.5×5.5 cm). After being placed for about 30 min at room temperature, the agarose gel would be ready to use.

The electrophoresis was performed at 120~430V for 15~20 min c. Reverse transcription of microRNA:

(I) Reaction system of reverse transcription

| | |
|---|---|
| Total RNA | 100 ng |
| Reverse transcription primer of microRNA | 1 μl(1 μM) |
| DEPC $H_2O$ | to 12.3 μl |
| The mixture was denatured at 65° C. for 5 min, then put into an ice bath for 5 min. | |
| 5 × 1$^{st}$ Buffer | 4 μl |
| 0.1M DTT | 2 μl |
| dNTPs | 0.5 μl(10 mM for each) |
| RNase Inhibitor | 0.2 μl(40 U/μl) |
| M-MLV | 1 μl(200 U/μl) |

The total volume of the system was 20 μl.

(II) Program of reverse transcription was: 16° C. for 30 min, 37° C. for 30 min, 70° C. for 10 min, then kept at 4° C.

d. RealTime PCR reaction of microRNA (I) Reaction system of microRNA RealTime PCR

| | |
|---|---|
| Template(cDNA) | 1 μl |
| $MgCl_2$ | 1.6 μl |
| Universal sense primer of microRNA | 0.6 μl(10 μM) |
| Primer Specific antisense primer | 0.6 μl(10 μM) |
| DNA Master SYBR Green I MIX | 2 μl |
| Nuclease-Free $H_2O$ | to 20 μl |

(II) Program of microRNA RealTime PCR

| | | | |
|---|---|---|---|
| Enzyme activation | 95° C., | 10 min | |
| Amplification reaction | 95° C., | 15 s | denaturation |
| | 60° C., | 30 s | annealing, elongation |
| | 74° C., | 3 s | fluorescence detection |
| for total of 40 cycles, | | | |
| Melting curve | 75~95° C. | | |

(III) Detection of RealTime PCR products by means of 1.5% non-denaturing (formaldehyde free) agarose gel electrophoresis

| | |
|---|---|
| miRNA real-time PCR product | 2~4 μl |
| 2 × Loading Buffer | 4 μl |

The total volume is about 6~8 μl.

Non-denaturing agarose gel: 1.2 g of agarose was added into 80 ml of 1×TBE Buffer, the mixture was heated to melt in a microwave oven and gently shaken to thoroughly mix the agarose (no suspending granules can be visually observed), 2 μl of EB (stock solution) was added when the mixture was cooled to about 60° C., the solution was mixed, and then poured into a gel casting module (15×5 cm). After being placed for about 30 min at room temperature, the agarose gel would be ready to use.

The electrophoresis was performed at 100V for 25~30 min.

(4) Analysis of Cell Invasion Ability

The principle is based on the characteristics of motility and directivity of tumor invasion. After contacting with the surface of matrix, tumor cells can move in a certain direction through a series of mechanisms.

a. For H446 and H1299 cells, matrigel was respectively diluted to 500 μg/mL and 1 mg/mL. 100 μl diluent was added into the upper chamber of the transwell insert of polycarbonate membrane (with 8 μm pores) and incubated for one hour at 37° C. in a 5% $CO_2$ incubator, and then the aqueous phase was aspirated, b. The well grown tumor cells were digested and re-suspended at a certain density after 48 hours post-transfection, c. 200 μl of cell suspension respectively containing $10 \times 10^4$ H446 cells or $5 \times 10^4$ H1299 cells was seeded in the upper chamber of each transwell insert, and 800 μl culture fluid containing 10% serum was added into the bottom chamber, then cells were cultured for 12 hours at 37° C. in a 5% $CO_2$ incubator, d. The chamber was taken out and the upper layer of cells without migration were scrapped off, e. Cells on the membrane were fixed with 70% methanol for 15 min, f. Cells were stained with 5% crystal violet (in methanol) for 20 min, then washed with distill water, g. Cells on the surface of bottom chamber were counted under a microscope, and statistically analyzed, and photographed at the same time.

(5) Analysis of Tumor Cell Adhesion a. Fibronectin was aspirated using precooling tips under aseptic operation, and diluted to 20 μg/mL, b. 50 μL diluted fibronectin was added into each well of a 96-well plate, c. The 96-well plate coated with fibronectin was dried in a sterile workbench, d. Cells were digested, centrifuged and resuspended with culture fluid containing 10% serum at 48 hours post-miRNA transfection, e. $5 \times 10^4$ cells were seeded into each well of the 96-well plate coated with fibronectin, and 5 parallel wells were set, f. After an incubation of 30, 60, 90 min or 30, 60 min respectively, H446 and H1299 cells were washed with PBS to remove non-adherent cells, and the medium was discarded in completely adhesion groups after 3 hours. Cells were fixed with 70% methanol for 10 min and dried at room temperature, then stained with 0.1% crystal violet for 20 min $OD_{570}$ was determined after decolorization with 10% SDS, which represents the adherent cells at different time points. A completely adhesion group was set up in each experimental group, g. The adhesion rate was calculated with residual cells, and the cell adhesion rate=(OD value of experimental group/OD value of completely adhesion group)×100%.

(6) Statistical Analysis

The experimental data were analyzed using SPSS10.0 software package (SPSS, Chicago, Ill.) with two-sided Student's t-test, $P<0.05$ as a significant difference.

2. Results (1) Transfection of Lung Cell Lines with Chemically Synthetic Mature miRNAs to Overexpress Target miRNA Transfection was performed using Lipofectamine 2000. For a single transfection, miR-886-3p, miR-150 or miR-AS-EGFP at a final concentration of 50 nM was used to transiently transfect H446 and H1299 cells, while for a co-transfection miR-886-3p and miR-150 at a final concentration of 37.5 nM or miR-AS-EGFP at a final concentration of 75 nM were used to transfect H446 and H1299 cells with miR-AS-EGFP as a control. At 48 hours post-transfection, cells were collected. And the expression levels of miR-886-3p and miR-150 were determined by real-time PCR. In the single transfection in H446 cell line, the expression level of miR-886-3p and miR-150 was increased by 2.5-fold and 2.9-fold respectively as compared to the control. In the co-transfection in H446 cell line, the expression level of miR-886-3p and miR-150 was increased by 1820.6-fold and 101.5-fold respectively as compared to the control. In the single transfection in H1299 cell line, the expression level of miR-886-3p and miR-150 was increased by 235.4-fold and 1723.3-fold respectively as compared to the control. In the co-transfection in H1299 cell line, the expression level of miR-886-3p and miR-150 was increased by 2736.3-fold and 2052.0-fold respectively as compared to the control. The results showed that the expression levels of miR-886-3p and miR-150 in H446 and H1299 cell lines increased significantly after the transfection, indicating that the transfection procedure and system was suitable for the corresponding research of overexpression of miRNA.

(2) Effect of High Expression of miR-886-3p and miR-150 on In Vitro Invasion Ability of Cells In vitro invasion ability of tumor cells was studied using Transwell invasion assays. H446 cells and H1299 cells were digested and resuspened with serum free RPMI 1640 at 24 hours post-transfection, and were respectively seeded at an amount of $1 \times 10^5$ cells and $5 \times 10^4$ cells in the upper chamber of a transwell insert, while 800 μl RPMI 1640 containing 10% serum was added in the bottom chamber, then the cells were cultured for 12 hours at °C 7 to allow their entry into the lower layer of 8 μm-pored polycarbonate membrane. Following staining with 0.5% crystal violet, cells stained purple were visible under a microscope (FIG. 5A, FIG. 6A), and cells on the lower surface of the polycarbonate membrane were counted. By calculation, the numbers of H446 cells transfected by miR-886-3p, miR-150 and miR-886-3p/miR-150 which had crossed the membrane were respectively 55.0%±8.5%, 65.7%±8.5%, 71.0%±8.5% of that of the control. The numbers of H1299 cells transfected by miR-886-3p, miR-150 and miR-886-3p/miR-150 which had crossed the membrane were respectively 73.6%±3.5%, 61.8%±11.1%, 83.7%±8.3% of that of the control. The results showed that the in vitro invasion ability of H446 and H1299 cells with high expression of miR-886-3p, miR-150 and miR-886-3p/miR-150 was obviously abated as compared to the control cells (FIG. 5B, FIG. 6B). And the difference was significant in the statistics analysis.

(3) Effect of High Expression of miR-886-3p and miR-150 on Extracellular Matrix Adhesion of H446 and H1299 Cell Lines Cell adhesion ability plays an important role in the metastasis of tumor cells. At 48 hours post-transfection, $5 \times 10^4$ H446 and H1299 cells were seeded into a fibronectin (20 μg/mL) extracellular matrix-coated 96-well plate. The cells were washed at various time points, and then the residual cells were adherent cells. The cells were fixed with 70% methanol for 10 min, stained with 0.1% crystal violet for 20 min. $OD_{570}$ value was determined after decolorization with 10% SDS. The adhesion rate was calculated, which reflected the adhesion ability to extracellular matrix. The results showed that the adhesion rate of H446 cells transfected by miR-NC, miR-886-3p, miR-150 and miR-886-3p/miR-150 respectively was 14.9%±0.9%, 11.3%±0.3%, 13.3%±0.1%, 11.4%±0.3% at 30 min; respectively was 45.1%±1.9%, 42.8%±2.2%, 45.1%±1.8%, 41.6%±1.1% at 60 min; respectively was 56.9%±1.0%, 49.0%±2.0%, 52.8%±0.5%, 47.6%±0.5% at 90 min (FIG. 7A). For H1299 cells transfected with miR-NC, miR-886-3p, miR-150 and miR-886-3p/miR-150, the adhesion rate respectively was 37.6%±1.5%, 34.7%±2.8%, 24.6%±3.0%, 23.4%±0.5% at 30 min; respectively were 47.1%±1.5%, 40.0%±2.1%, 36.6%±2.2%, 29.9%±4.2% at 90 min (FIG. 7B). As compared to the control cells, the adhesion rates of H446 and H1299 cells transfected with miR-886-3p, miR-150 and miR-886-3p/miR-150 were all reduced, and the difference was significant by a statistics analysis. The results showed that the extracellular matrix adhesion ability of H446 and H1299 cells with high expression of miR-886-3p, miR-150 and miR-886-3p/miR-150 was obviously diminished.

REFERENCES

Fischer B, Marinov M, Arcaro A (2007). "Targeting receptor tyrosine kinase signalling in small cell lung cancer (SCLC): What have we learned so far?" Cancer Treatment Reviews 33: 391-406.

Bonner J A, Harari. P M, Giralt J, et al (2006). "Radiotherapy plus cetuximab for squamous-cell carcinoma of the head and neck." N Engl J Med 354: 567-578.

Xiao C, Calado D P., Galler G, et al (2007). "MiR-150 Controls B Cell Differentiation by Targeting the Transcription Factor c-Myb." Cell 131: 146-159.

Sekine I, Yamamoto N, Kunitoh H, et al (2004). "Treatment of small cell lung cancer in the elderly based on a critical literature review of clinical trials." Cancer Treatment Reviews 30: 359-368.

Morita T, Sugano H. (1990). "A statistical analysis of lung cancer registered in the Annual of Pathological Autopsy Cases in Japan between 1958 and 1987, with special reference to the characteristics of lung cancer in Japan." Acta Pathol Jpn 40: 665-675.

Nilsson B, Sjölund K, Kindblom L G, et al (2007). "Adjuvant imatinib treatment improves recurrence-free survival in patients with high-risk gastrointestinal stromal tumours (GIST)." Br J Cancer 96: 1656-1658.

Parkin D M, Pisani P., Ferlay J (1999). "Estimates of the worldwide incidence of major cancers in 1990." Int J Cancer 80: 827-841.

Sandler A B (2003). "Chemotherapy for small cell lung cancer." Semin Oncol 30: 9-25.

The invention claimed is:

1. A composition, comprising a therapeutically effective amount of a microRNA molecule of microRNA-150 having the sequence shown as SEQ ID NO:1 and a microRNA molecule microRNA-886-3p having the sequence shown as SEQ ID NO:2.

2. The composition as claimed in claim 1, further including a pharmaceutically acceptable carrier.

3. A device containing the composition as claimed in claim 1 used for the detection of mammalian and human lung cancer prognosis.

4. The device as claimed in claim 3, wherein the lung cancer is small cell lung cancer.

5. The device as claimed in claim 3, wherein the device is a gene chip or a reagent kit.

6. A method for inhibiting mammalian and human lung cancer transformation, comprising administrating a therapeutically effective amount of the composition of claim 1.

7. The method of claim 6, wherein the lung cancer is small cell lung cancer.

* * * * *

SEQUENCE LISTING

```
<160> NUMBER OF SEQ ID NOS: 7

<210> SEQ ID NO 1
<211> LENGTH: 22
<212> TYPE: RNA
<213> ORGANISM: Homo sapiens

<400> SEQUENCE: 1
ucucccaacc cuuguaccag ug                                              22

<210> SEQ ID NO 2
<211> LENGTH: 21
<212> TYPE: RNA
<213> ORGANISM: Homo sapiens

<400> SEQUENCE: 2
cgcgggugcu uacugacccu u                                               21

<210> SEQ ID NO 3
<211> LENGTH: 16
<212> TYPE: DNA
<213> ORGANISM: Artificial Sequence
<220> FEATURE:
<223> OTHER INFORMATION: Synthetic microRNA Reverse Transcription Primer

<400> SEQUENCE: 3
gtgcagggtc cgaggt                                                     16

<210> SEQ ID NO 4
<211> LENGTH: 50
<212> TYPE: DNA
<213> ORGANISM: Artificial Sequence
<220> FEATURE:
<223> OTHER INFORMATION: Synthetic microRNA Universal Sense Primer, for
      MicroRNA150

<400> SEQUENCE: 4
gtcgtatcca gtgcagggtc cgaggtattc gcactggata cgaccactgg               50

<210> SEQ ID NO 5
<211> LENGTH: 50
<212> TYPE: DNA
<213> ORGANISM: Artificial Sequence
<220> FEATURE:
<223> OTHER INFORMATION: Synthetic microRNA Universal Sense Primer, for
      MicroRNA886-3p
```

```
<400> SEQUENCE: 5
gtcgtatcca gtgcagggtc cgaggtattc gcactggata cgacaagggt                50

<210> SEQ ID NO 6
<211> LENGTH: 20
<212> TYPE: DNA
<213> ORGANISM: Artificial Sequence
<220> FEATURE:
<223> OTHER INFORMATION: Synthetic Antisense Primer, for MicroRNA150

<400> SEQUENCE: 6
gtctcccaac ccttgtacca                                                 20

<210> SEQ ID NO 7
<211> LENGTH: 19
<212> TYPE: DNA
<213> ORGANISM: Artificial Sequence
<220> FEATURE:
<223> OTHER INFORMATION: Synthetic Antisense Primer, for MicroRNA886-3p

<400> SEQUENCE: 7
cacgcgggtg cttactgac                                                  19
```